US00PP09300P

United States Patent [19]

Dehan

[11] Patent Number: Plant 9,300

[45] Date of Patent: Sep. 26, 1995

[54] ASTER PLANT NAMED 'SUNTANA'

[75] Inventor: Klara Dehan, Holon, Israel

[73] Assignee: Danziger - "Dan" Flower Farm, Post Beit Dagan, Israel

[21] Appl. No.: 291,698

[22] Filed: Aug. 16, 1994

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A new and distinct cultivar of Aster plant named Suntana, characterized by its purple ray floret color, relatively small diameter, double flowers; strong and rigid stems, each of which carries many flowers; excellent branching, producing a spreading plant shape; and early flowering.

1 Drawing Sheet

The present invention comprises a new and distinct cultivar of Aster plant, botanically known as *Aster ericoides,* hereinafter referred to by the cultivar name Suntana.

The new cultivar was originated from a cross made in a controlled breeding program by the inventor Klara Dehan in Mishmar Hashiva, Israel.

Both the female, or seed, and the male, or pollen parents were cultivars of *Aster ericoides,* the breeding numbers of which were unrecorded and are unknown at this time. Both parents are proprietary lines used exclusively for breeding.

Suntana was discovered and selected by the inventor as a flowering plant within the progeny of the stated cross in a controlled environment in Mishmar Hashiva, Israel. Asexual reproduction of the new cultivar by leaf cuttings performed by the inventor at Mishmar Hashiva, Israel has demonstrated that the combination of characteristics as herein disclosed for the new cultivar are firmly fixed and retained through successive generations of asexual reproduction.

Suntana has not been observed under all possible environmental conditions. The phenotype may vary somewhat with variations in environment such as temperature, light intensity and daylength, without, however, any variation in genotype. The following observations, measurements and values describe the new cultivar as grown in Mishmar Hashiva, Israel under conditions which closely approximate those generally used in commercial practice.

The following traits have been repeatedly observed and are determined to be basic characteristics of Suntana which in combination distinguish this Aster as a new and distinct cultivar:

1. Unique intense purple ray floret color with light yellow center.
2. Relatively small diameter, double flowers.
3. Strong and very heavy stems, each of which carries many flowers.
4. Excellent branching, producing a spreading plant shape.
5. Early flowering.
6. Can be grown in garden bedding programs or in greenhouse cut spray programs.

The accompanying color photographic drawing illustrates a portion of a typical specimen plant of the new cultivar, with many buds, partially open, and completely open flowers being illustrated. The flowers are shown enlarged relative to true size. The photo does not accurately depict true ray and disc floret colors, the true color values for which are noted below.

In the following description, color references are made to the Royal Horticultural Society Colour Chart (RHS), except where general colors of ordinary significance are referred to. Color values were taken in the morning in Mishmar Hashiva, Israel.

Classification:

*Botanical.*—*Aster ericoides* Hybrid cv. Suntana.

*Commercial.*—Daisy-like spray and garden variety.

Parentage

*Male parent.*—Unknown seedling of *Aster ericoides.*

*Female parent.*—Unknown seedling of *Aster ericoides.*

Propagation: The new cultivar holds its distinguishing characteristics through successive propagations by leaf cuttings.

INFLORESCENCE

A. Capitulum:

*Form.*—Daisy, round, generally flat.

*Type.*—Double, with more than 40 total petals appearing in 2–3 rows.

*Diameter across face.*—2.0 to 2.7 cm. depending on the growing season. The diameter is larger in the winter.

B. Corolla of ray florets:

*Color (general tonality from a distance of three meters).*—Red-purple.

*Color (upper surface).*—77A.

*Color (under surface).*—87A.

*Shape.*—Petals are generally narrow and oblong, with apex rounded; straight to slightly concave. This produces a relatively fuller appearance.

*Size.*—The petals are approximately 10 mm. long and 3–4 mm. wide, relatively wide compared to other cultivars of the species.

C. Corolla of disc florets:

*Color (mature).*—2C.

*Color (immature).*—2C.

*Diameter of disc.*—1 cm.

D. Flowering period: When field grown in natural season, plants planted in June will flower in September. In winter greenhouse production, preferred culture includes approximately four weeks of long-day treatment after pinching until the stems elongate to approximately 10 cm, followed by short days. With short day treatment, Suntana will flower from the start of short days in approximately 5 weeks in the fall and 7 weeks in the winter.

E. Reproductive organs:

*Androecium.*—Stamens present on both ray and disc florets; filaments are noticeably elongated in fully open flower, providing a distinctive balanced appearance with surrounding petals; pollen is yellow and found only in the winter season in Israel.

*Gynoecium.*—Present on disc florets; green in color.

F. Fertility: Has not been ascertained.

G. Receptacle: The receptacle, involucre and phyllaries are normal for plants of the species.

PLANT

A. General appearance: Excellent branching and very heavy stems result in a great abundance of small red-purple flowers; medium to tall in height, reaching a main stem height of 1–1.2 meters; height depends largely on light conditions. After repeated crops, base of plant loses some of its stability but does not become woody.

B. Foliage:

*Color.*—147A.

*Shape.*—Linear, without stipules, with occasional downward reflexing at the tip.

*Size.*—145 mm long and 11 mm wide near bottom of plant; leaves near top of plant are 35 mm long and 3 mm wide.

*Margin.*—Entire.

*Arrangement.*—Alternate, with angle acute.

I claim:

1. A new and distinct cultivar of Aster plant named Suntana, as illustrated and described.

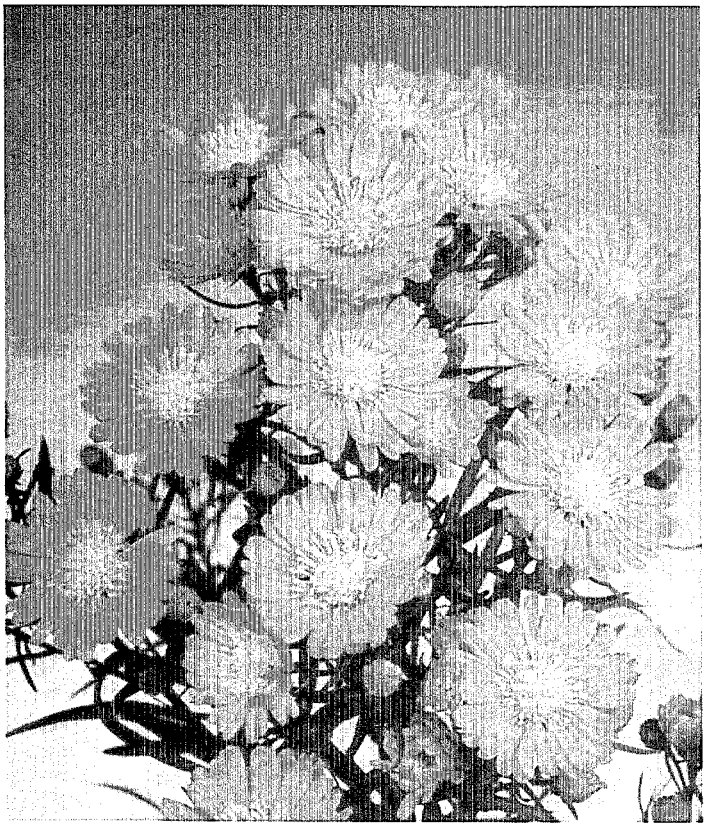

* * * * *